US009572538B2

(12) United States Patent
Sitzman et al.

(10) Patent No.: US 9,572,538 B2
(45) Date of Patent: Feb. 21, 2017

(54) SYSTEM AND METHOD FOR PERFUSION-BASED ARRHYTHMIA ALARM EVALUATION

(71) Applicant: General Electric Company, Schenectady, NY (US)

(72) Inventors: David Alan Sitzman, Milwaukee, WI (US); Bruce Arnold Friedman, Jasper, GA (US); Sahika Genc, Niskayuna, NY (US); Kalpit Vikrambhai Desai, Bangalore (IN); Michael Anthony Lexa, Niskayuna, NY (US); Brett Matthews, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 398 days.

(21) Appl. No.: 14/189,237

(22) Filed: Feb. 25, 2014

(65) Prior Publication Data
US 2015/0238151 A1    Aug. 27, 2015

(51) Int. Cl.
*A61B 5/02*    (2006.01)
*A61B 5/00*    (2006.01)
(Continued)

(52) U.S. Cl.
CPC ............... *A61B 5/746* (2013.01); *A61B 5/021* (2013.01); *A61B 5/0464* (2013.01); *A61B 5/7221* (2013.01); *A61B 5/14542* (2013.01)

(58) Field of Classification Search
CPC ......... A61B 5/00; A61B 5/024; A61B 5/0452; A61B 5/746; A61B 5/7221; A61B 5/0464; A61B 5/021; A61B 5/14542; A61B 5/046; A61B 5/0468; A61B 5/0472
See application file for complete search history.

(56) References Cited

U.S. PATENT DOCUMENTS

| 5,473,948 A * | 12/1995 | Moss ...................... G01S 15/58 600/454 |
| 7,218,966 B2 * | 5/2007 | Haefner ........... A61B 17/32006 607/17 |

(Continued)

FOREIGN PATENT DOCUMENTS

| EP | 1724684 A1 | 11/2006 |
| WO | 2012125135 A1 | 9/2012 |

OTHER PUBLICATIONS

Aboukhalil, Anton et. al, "Reducing false alarm rates for critical arrhythmias using the arterial blood pressure waveform", Journal of Biomedical Informatics, vol. 41, Issue 3, Jun. 2008, (pp. 442-451, 10 pages total).

(Continued)

*Primary Examiner* — Navin Natnithithadha
*Assistant Examiner* — Eric Messersmith
(74) *Attorney, Agent, or Firm* — Buckley, Maschoff & Talwalkar LLC

(57) ABSTRACT

A method of prioritizing arrhythmia alarms based on one patient's perfusion level includes receiving arterial blood pressure, electrocardiogram heart rate, and arterial pulse rate values of the one patient during a same time window. Analyzing the set of blood pressure values to determine if an arrhythmia event is indicated, where if an arrhythmia event is indicated, the method includes calculating a systolic blood pressure (SBP) ratio, comparing the SBP ratio to a first predetermined threshold, and if the SBP ratio is less than or equal to the first predetermined threshold, then activating a non-perfusion alarm. If the SBP ratio is greater than the first predetermined threshold, then calculating a standard deviation of a rate differential between the heart rate and the pulse rate values, and if the standard deviation is greater than a second predetermined threshold, then activating the non- (Continued)

perfusion alarm. A system and non-transitory computer media is also presented.

19 Claims, 4 Drawing Sheets

(51) Int. Cl.
   *A61B 5/021* (2006.01)
   *A61B 5/0464* (2006.01)
   *A61B 5/145* (2006.01)

(56) References Cited

U.S. PATENT DOCUMENTS

| | | | |
|---|---|---|---|
| 7,828,739 B2 | 11/2010 | Arnold | |
| 8,031,076 B2 | 10/2011 | Sachanandani et al. | |
| 8,140,154 B2 | 3/2012 | Donnelly et al. | |
| 8,364,248 B2 | 1/2013 | Zhang | |
| 8,639,324 B2 | 1/2014 | Elferri et al. | |
| 2001/0051773 A1* | 12/2001 | Oka | A61B 5/02125 600/483 |
| 2005/0234321 A1* | 10/2005 | Funahashi | A61B 5/00 600/407 |
| 2009/0163774 A1 | 6/2009 | Thatha et al. | |
| 2009/0292332 A1* | 11/2009 | Li | A61B 5/0464 607/5 |
| 2010/0241182 A1* | 9/2010 | Whitman | A61B 5/0215 607/5 |
| 2011/0201945 A1 | 8/2011 | Li et al. | |
| 2012/0179011 A1* | 7/2012 | Moon | A61B 5/7207 600/324 |
| 2012/0232416 A1* | 9/2012 | Gilham | A61B 5/7246 600/515 |
| 2013/0030307 A1* | 1/2013 | Rajan | A61N 1/3925 600/479 |

OTHER PUBLICATIONS

Deshmane, Anagha Vishwas "False Arrhythmia Alarm Suppression Using ECG, ABP, and Photoplethysmogra", 2009, Department of Electrical Engineering and Computer Science, Aug. 21, 2009, (pp. 1-93, 93 pages total).

* cited by examiner

SYSTEM AND METHOD FOR PERFUSION-BASED ARRHYTHMIA ALARM EVALUATION

BACKGROUND

To manage cardiac disorders and irregularities it is useful to identify and characterize a patient's cardiac arrhythmia episodes. Conventionally, electrocardiogram (ECG) and intra-cardiac electrogram signals can be analyzed to detect and diagnose arrhythmia events. Conventional systems for cardiac arrhythmia identification and analysis utilize ECG data only and do not take into account hemodynamic changes that are in general considered by the clinical expert to access the patient state and determine whether there is a need for action (such as medication and catheter ablation) to reverse the adverse condition.

Early recognition of arrhythmias is an important contributor to manage cardiac disorders and irregularities. Currently cardiac arrhythmia monitoring and identification is based on waveform shapes and analysis of time domain parameters (e.g., P wave, QRS complex, ST segment, T wave, etc.). Proper arrhythmia identification and treatment using such conventional systems still require a systemic approach that incorporates vital signs such as arterial blood pressure, patient medical history including medications and surgeries, and demographics.

Other conventional systems also interpret electrophysiological signals using mathematical analysis (e.g., frequency analysis, symbolic complexity analysis and nonlinear entropy evaluation). Other existing approaches analyze signal characteristics (e.g., waveform amplitude, power spectrum, etc.), but might not be able to discern small changes in a portion of the cardiac cycle.

Prior methods to identify arrhythmia events can be based on hard-coded thresholds obtained by an understanding of the physiological system. These thresholds are from a limited group of patients. Threshold-based methods are widely adopted in industry due to ease of implementation on the bed-side. However, the threshold-based methods generate a lot of false alarms that may cause an unnecessary burden on nurses and clinicians result in alarm fatigue. Even when arrhythmia events are correctly identified, the impact of these events on the ability of the heart to properly perfuse the tissues in the body is not ubiquitously monitored.

DETAILED DESCRIPTION

Figure 1:
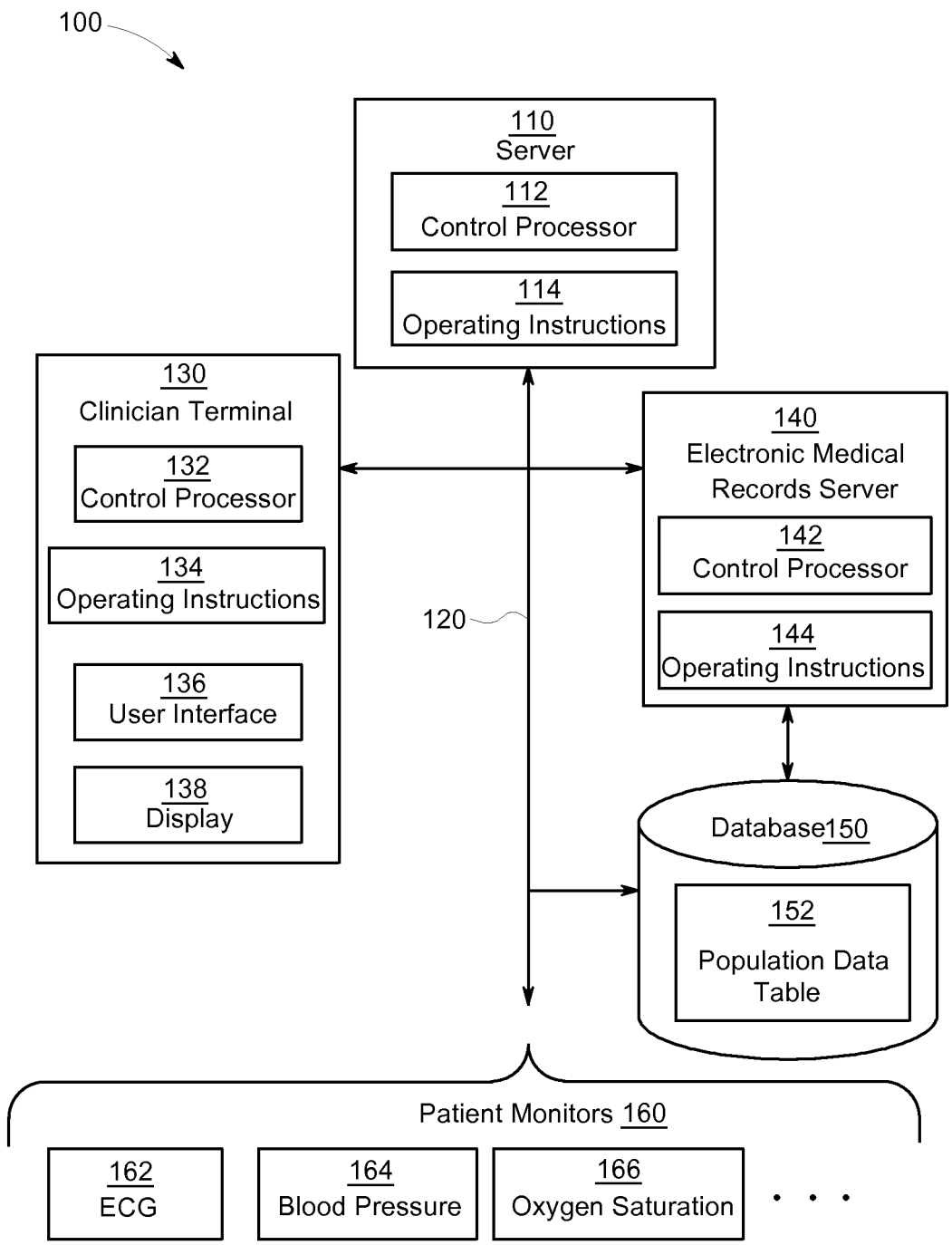
FIG. 1 depicts a system in accordance with some embodiments.

Systems and method in accordance with embodiments evaluate arrhythmia alarms based on a perfusion level calculated from multiple parameters (e.g., ECG, blood pressure, oxygen saturation, etc.) collected from multiple sources including, but not limited to, patient monitors, electronic medical records, and/or manual clinical annotations in an acute or intensive care environment. By evaluating arrhythmia alarms based on perfusion level, the alarms can be prioritized so that clinicians can focus on the actionable events that require a life-support device or surgery and reduce false alarms to improve confidence in the patient monitors. In one implementation, the evaluation of arrhythmia alarms can include a four layer approach.

In accordance with embodiments, the first layer includes an assessment of the signal quality detected for each parameter to be utilized in determining the patient's perfusion level. In one implementation, the signal quality can be an indicator between 0 and 1. If the signal quality for each parameter is above an acceptable level, then the signals are passed to the second layer of the approach.

For example, the quality of an ECG signal can be assessed by looking at spectral energy distribution, higher order moments and inter-channel/inter-algorithm agreement. One approach can use an inverse Dower transform to identify time-frequency features of the ECG signal. Another approach for signal assessment can identify baseline drift, flat line, QRS-artifact, spurious spikes, amplitude step changes, and other noise using single-condition decision rules for classifying thresholds. The ECG signal can be assessed, in general, by examining four sources of quality loss—e.g., missing signal or reduced energy of the QRS; presence of high amplitude and steep artifacts; baseline drift; power line interference; and high-frequency and electromyographic noise.

Assessment of an arterial blood pressure signal quality can require an adaptive filtering approach that accounts for artifact types. One approach determines a signal quality index (SQI) based on a combination of two signal quality measures weighted together. One index measures morphological normality, and the other degradation due to noise. These artifact types can have differing effects on systolic, diastolic and mean ABP estimates. However, for most artifact types, diastolic ABP estimates are less noise-sensitive than mean ABP estimates, which in turn are more robust than systolic ABP estimates. The SQI can provide error bounds for both HR and ABP estimates, even in the presence of high levels of persistent noise and artifact, and during extreme bradycardia and tachycardia. Differences in error between artifact types, measurement sensors and the quality of the source signal can be factored into physiological estimation using an unbiased adaptive filter, signal innovation and signal quality measures.

In the second layer, a multitude of trends are extracted from the good quality signals. The trends can describe one or more properties of the good quality waveform signals. One of the most commonly utilized trends is the heart rate from an ECG signal. One of the unique trends is to calculate a pulse rate from arterial blood pressure (ABP) signal that describes the mechanical functioning of the heart as a pump.

In conventional monitoring, heart rate from an ECG signal is utilized since it is more robust. However, discrepancies between heart rate measurements from ECG and pulse rate from ABP monitors can indicate a loss in synchrony of electrical signals that trigger the heart muscles to contract and/or relax and the mechanical pumping activity of the heart to provide blood to the aorta and the rest of the vascular system in the body.

In the third layer, statistical and temporal properties of trends are utilized to build features that differentiate arrhythmias based on their perfusion level. The differential can be classified as, for example, low, medium, and high perfusion levels.

In the fourth layer, a model for perfusion level is generated from the training data utilizing a classification tree approach that ranks the various statistical and temporal features in their statistical significance based on the training data. In one implementation, the training data is dynamic. The training data can begin with an initial data set of historical data, and the perfusion level model can be updated and adapted when/if new training data becomes available from patient monitors, electronic medical records, and/or manual clinical annotations.

In accordance with embodiments, the evaluation of arrhythmia alarms can be based on the hemodynamic changes observed in the ABP waveform which may be characterized as asynchrony between the electrical heart muscle pulsations, the mechanical pumping capability of the heart, a drop in systolic blood pressure before, during, and after the occurrence of pacing-induced arrhythmia. For example, the higher the asynchrony and the drop in systolic blood pressure, the lower the patient's perfusion level, hence, the higher the possibility that the arrhythmia is life-threatening. In addition to asynchrony and drop in the systolic blood pressure, statistical and temporal measures of the ECG and ABP morphologies (e.g., mean and standard deviation of systolic and diastolic pressures, pulse pressures, duration and frequency of the arrhythmias, etc.) can also be utilized to assess the criticality and/or severity of the degree in perfusion and the patient's ability to withstand disturbances in the electrical and pumping activity of the heart when an arrhythmia occurs.

FIG. 1 depicts distributed computer system 100 for prioritizing arrhythmia alarms in accordance with an embodiment. System 100 includes server 110, electronic communication network 120, clinician terminal 130, electronic medical record (EMR) server 140, database 150, and patient monitors 160. Dedicated hardware, software modules, firmware, and/or a combination thereof can be used to implement components of system 100.

Server 110 can include control processor 112 and operating instructions 114. Control processor 112 can be a processing unit, a field programmable gate array, discrete analog circuitry, digital circuitry, an application specific integrated circuit, a digital signal processor, a reduced instruction set computer processor, etc. The control processor may access operating instructions 114, which can be a computer application program stored in internal memory, or stored in external memory, coupled to the control processor. The computer program application may include program code or executable program instructions that when executed may instruct and/or cause control processor 112 to perform methods described herein. Server 110 may include internal memory (not shown) connected to control unit 112. Internal memory represents both volatile and non-volatile memory devices. Non-volatile external memory may be connected to control unit 112 via an input/output (I/O) port (not shown). The non-volatile memory can be any mass storage memory technology (e.g., flash drives, hard disk drives, optical disc drives, magneto-optical disc drives, holographic, bubble, etc.)

Server 110 can interconnect and communicate with other components of system 100 via electronic communication network 120. In an embodiment, server 110 can be located remotely, for example as a remote server. Electronic communication network 120 can be, can comprise or can be part of, a private internet protocol (IP) network, the Internet, an integrated services digital network (ISDN), frame relay connections, a modem connected to a phone line, a public switched telephone network (PSTN), a public or private data network, a local area network (LAN), a metropolitan area network (MAN), a wide area network (WAN), a wireline or wireless network, a local, regional, or global communication network, a virtual private network, an enterprise intranet, any combination of the preceding and/or any other suitable electronic communication network. It should be recognized that techniques and systems disclosed herein are not limited by the nature of network 120.

Clinician terminal 130 can be any type of computing device suitable for use by an end user (e.g., a personal computer, a workstation, a thin client, a netbook, a notebook, tablet computer, smart phone, handheld computing device, etc.). System 100 can support operation of multiple clinician terminals across network 120.

The clinician terminal can include control processor 132 and operating instructions 134. Clinician terminal 130 can include a dynamic, interactive user interface that is presented on display 138.

Electronic medical records (EMR) server 140 can be located remotely from other components of system 100. EMR server 140 can be in communication with database 150 directly (e.g., via a local connection), and/or across electronic communication network 120.

Database 150 can be any physical memory system for storing data. These physical memory systems may comprise a portion, an entirety, or several, of any type of non-volatile mass storage memory technology (e.g., hard disk drives, optical disc drives, magneto-optical disc drives, holographic memory, bubble memory, etc.).

Figure 2:
FIG. 2 depicts a data table in accordance with some embodiments.

Database 150 can include population data table 152. FIG. 2 depicts the contents of population data table 152 in accordance with an embodiment. This depiction of the data table is for discussion only, it should be recognized that the organization of data in the data table can be varied (e.g., flat data table, multi-dimensional, etc.).

Population data table 152 can include patient identification column 153. Patient identification column 153 contains string data with patient identifying information (e.g., name, patient number, etc.). This column contains identifying information for each arrhythmia event (i.e., by arrhythmia id) that is logged for that patient. By way of example, there are two patients identified in column 153 (patient1 and patient2). Patient1 has experienced two arrhythmia events (arrhythmia1 and arrhythmia2), while patient 2 has experienced only one arrhythmia event.

Systolic Blood Pressure (SBP) ratio column 154 includes numeric data. The SBP ratio is the ratio of the delta systolic blood pressure and the systolic blood pressure prior to an event, where the event is an arrhythmia episode, and the delta is the difference between the maximum and minimum SBP during the event.

Standard Deviation column 155 includes numeric data representing the standard deviation of the heart rate differential between a mechanically measured pulse rate (measured from arterial blood pressure (ABPHR)) and an electrically measured heart rate (obtained from an ECG (ECGHR)). Annotation column 156 includes string data representing information from a clinician and/or from an EMR dataset whether the alarm is true or false. The annotation column is later used for supervised learning of models to correctly determine perfusion and/or evaluation of arrhythmia within clinical context. For instance, the anecdotal information can be a "1" or "0", or a "T" or "F" to indicate anecdotally whether the particular episode for this patient was, or was not, a non-perfusion event.

Figure 3A:
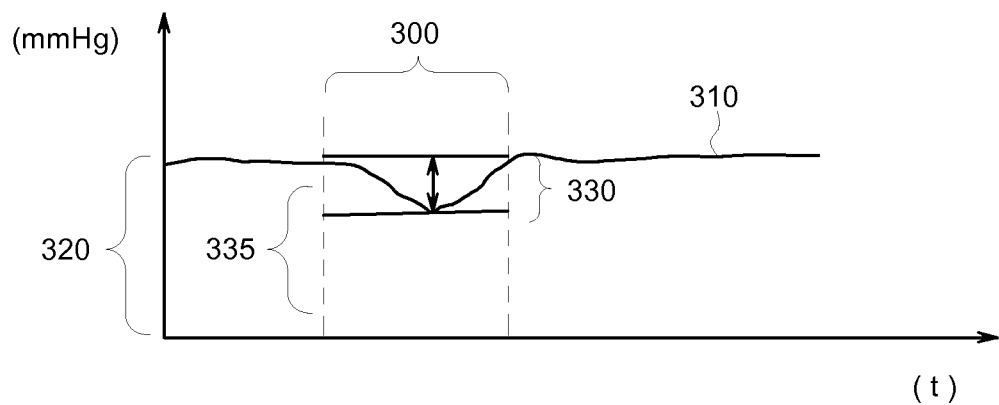
FIG. 3A depicts a plot of systolic blood pressure over time.

FIG. 3(A) depicts a representative plot of SBP over time for a mammalian patient. An arrhythmia can occur during event 300. Prior to the occurrence of event 300, the SBP is at a first level 320. During the event, the patient's SBP can decrease from the first level that is present prior to the event. The SBP difference magnitude 330 between first level 320 and SBP event minimum level 335 is one term in calculating SBP ratio 154 for this event. The other term in the ratio is SBP first level 320.

Figure 3B:
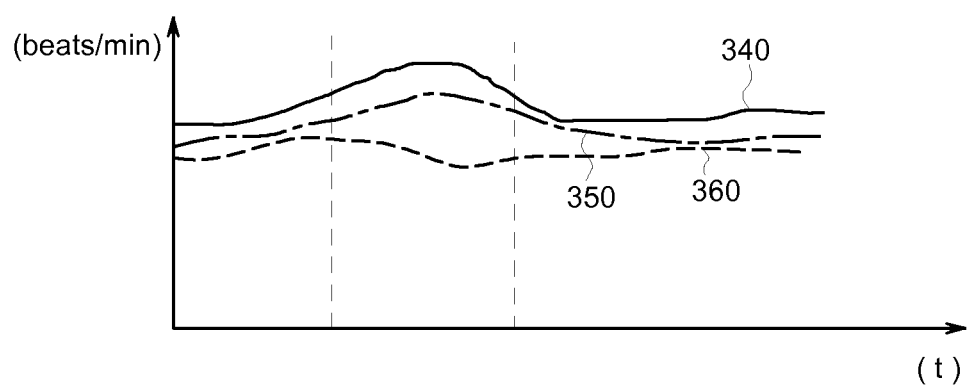
FIG. 3B depicts plots of heart and pulse rate measurements over time.

FIG. 3(B) depicts a representative plot of heart and pulse rate measurements over time for an adult human patient. FIGS. 3(A) and 3(B) are aligned in time, so that heart rate measurements 340, 350, 360 are measured during event 300. Heart rate measurement 340 is representative of an electrically measured heart rate from an ECG. Pulse rate measurement 350 is representative of mechanically measured arterial blood pressure (ABP).

In accordance with an implementation, a plethysmogram (i.e., a pulse oximeter) is a measure of changes in blood volume. The plethysmogram signal, like the ABP signal, is pulsatile and can be used to determine the mechanical pulse rate. Changes in the plethysmogram amplitude can be used to assess changes in perfusion during an arrhythmia. Changes in the oxygen saturation value derived from the plethsymogram could also be used to assess changes in perfusion (if the oxygen saturation is not filtered).

As depicted in FIG. 3B, during event 300 ECG plot 340 and the ABP plot 350 both increase. The synchronicity between the electrical measurement and the mechanical measurement indicate that the heart is responding to the electrical nerve impulses commanding the beat. This synchronicity is an indication that the patient is likely perfused, and that the arrhythmia event could be classified as less critical.

However, ABP plot 360 illustrates a pulse rate that decreases during event 300, and is not synchronous with ECG plot 340. This asynchronous behavior between the electrical nerve impulses and the arterial pulse rate is an indication that the heart muscles and/or systemic arteries are not responding to the electrical commands, and that the patient can be non-perfused. These asynchronous readings are an indication that the arrhythmia event could be classified as more critical depending on its level (i.e., in general, it is known and expected that pacing-induced tachycardia is associated with hemodynamic alterations because of the limited duration of diastole).

Figure 4:
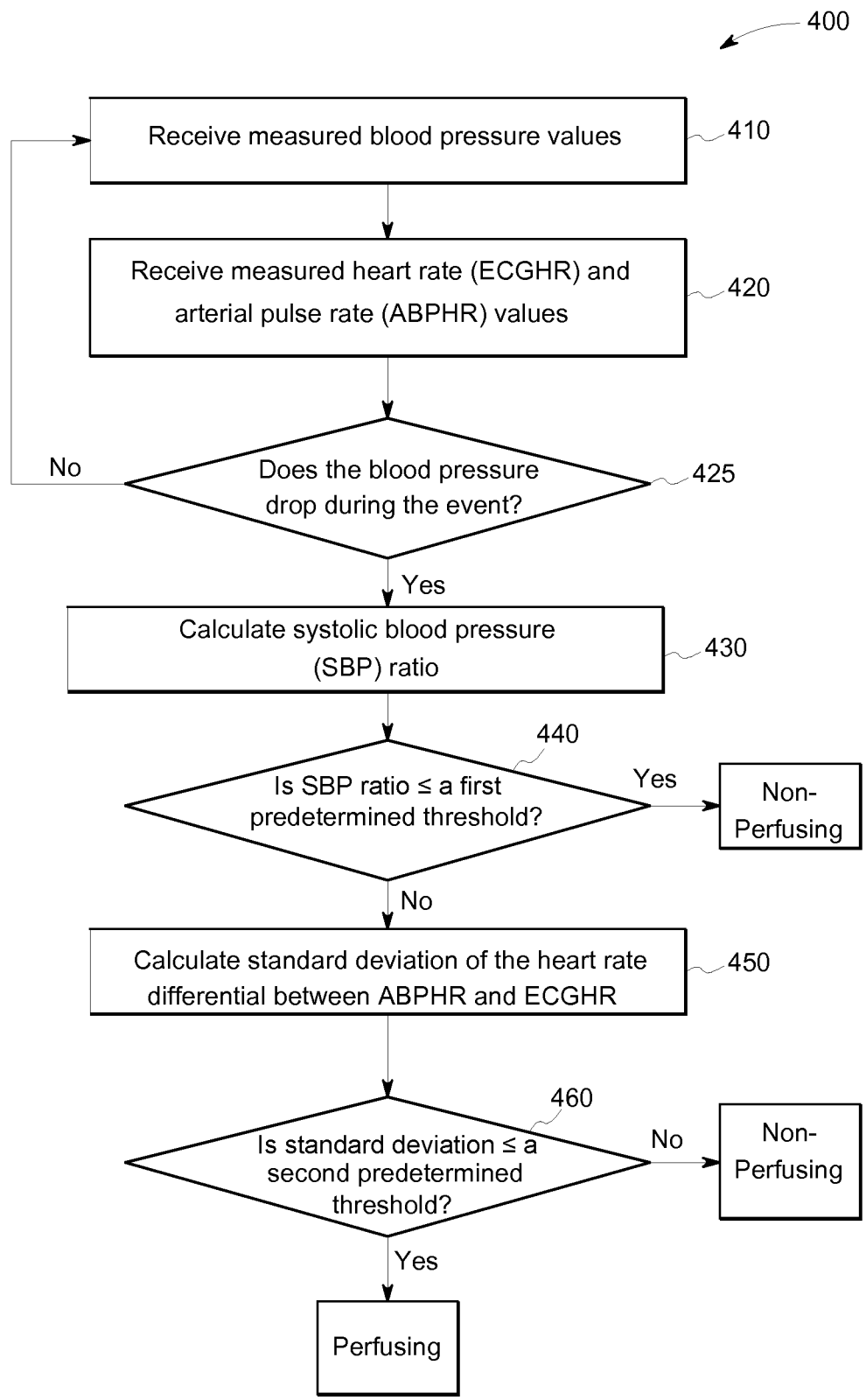
FIG. 4 depicts a process flow diagram in accordance with some embodiments.

FIG. 4 depicts a flow diagram of process 400 for evaluating arrhythmia alarms based on asynchrony between the ECG-measured heart rate and the ABP-measured pulse rate in accordance with some embodiments. Process 400 is an embodiment of a model generated by a Machine Learning algorithm trained on the above mentioned dynamic training data with clinical annotations of level of hemodynamic impact associated with a pacing-induced arrhythmia. For example, the alarm evaluation can be used to prioritize the criticality and/or severity of the patient's condition. The patient's arterial blood pressure values are received in a memory, step 410. Values of both a heart rate determined from the ECG signal and a pulse rate determined from a blood pressure or blood volume signal are also received in a memory, step 420.

The arterial blood pressure signal is analyzed to determine if there is an ongoing (or was) clinically-actionable arrhythmia event, step 425. The determination is made based on whether there is a drop in the arterial blood pressure during the event. If there was not a clinically-relevant arrhythmia event, process 400 returns to step 410.

If a determination is made that there is a clinically-relevant arrhythmia event (step 425), process 400 continues to step 430. A systolic blood pressure ratio based on the measured samples stored in memory is calculated at step 430. The SBP ratio is the ratio of the systolic blood pressure 320 (FIG. 3) prior to an event and the delta systolic blood pressure 320 (FIG. 3). In accordance with some embodiments, a systolic ratio can also be computed from the amplitude of the plethysmogram.

If the SBP ratio is less than or equal to a first pre-determined threshold value, step 440, than the patient can be considered non-perfused. An alarm should sound for this arrhythmia event. The severity of the alarm (e.g., low, medium, and high) can be determined from the model generated by the Machine Learning algorithm that utilizes features extracted from statistical and temporal trends based on data stored in the population data table and/or EMR sources. In addition to asynchrony, statistical and temporal measures (e.g., mean and standard deviation of systolic and diastolic pressures, pulse pressures, duration and frequency of the arrhythmias, etc.) can also be utilized to assess the criticality and/or severity of the non-perfusion and the patient's ability to withstand disturbances in the electrical and pumping activity of the heart when an arrhythmia occurs.

If the SBP ratio is greater than the first pre-determined threshold, than process 400 continues to step 450. A standard deviation of the heart rate differential between ABPHR and ECGHR is calculated at step 450. At step 460, this standard deviation is compared to a second pre-determined threshold. If the standard deviation is less than or equal to the second pre-determined threshold value, than the patient can be considered perfused. If the standard deviation is greater than the second pre-determined threshold, than the patient can be considered non-perfused. An alarm should sound for this arrhythmia event. The severity of the alarm (e.g., low, medium, and high) can be determined from statistical and temporal trends based on data stored in the population data table and/or EMR sources. In addition to asynchrony, statistical and temporal measures (e.g., mean and standard deviation of systolic and diastolic pressures, pulse pressures, duration and frequency of the arrhythmias, etc.) can also be utilized to assess the criticality and/or severity of the non-perfusion and the patient's ability to withstand disturbances in the electrical and pumping activity of the heart when an arrhythmia occurs.

Although based on different data sets (i.e., sampling of blood pressure and heart rate), both the first pre-determined threshold and the second pre-determined threshold are based on data extracted from signals assessed to have good quality. The thresholds can be determined by analyzing statistical and temporal trends based on data stored in the population data table 152 (FIG. 1) and/or EMR sources. System 100 for evaluating arrhythmia alarms can include operating instructions in the form of executable program code, or instruction, that cause a control processor to execute program instructions for an algorithm generated by a supervisory machine learning technique using the training set and cross-validating on the test set from the data stored in the population data table. This process generated by the supervisory machine learning technique can be dynamic, in that the process can determine updated thresholds as the data available is expanded. The thresholds can be updated at regular intervals, by command received from a user, and/or even continually.

The supervisory learning algorithm can analyze the dataset to determine pattern classification and clustering of population samples so that the hemodynamic impact of a patient's asynchronous ECGHR and ABPHR during an arrhythmia event can be more accurately predicted.

To determine pattern classification, in accordance with some embodiments, each instance (i.e., a row in data table 152 (FIG. 2)) can be assigned to one of a pre-defined class—for example, low, medium, or high impact. Several supervisory learning based classification methods have been explored—Conditional Inference Trees, Support Vector Machines, and Random Forests.

Random Forests is a Machine Learning method that can learn an ensemble of trees for a given classification or regression problem. This algorithm can include two layers of randomization on top of the Classification and Regression Tree (CART) at its core: The training examples used to learn each tree are randomly selected using a bootstrap sample of the whole training set. At each node, the set of features evaluated to make further splits is randomly chosen from the set of all available features. The prediction of the "forest" is computed by aggregating prediction of each tree in the ensemble—i.e., the majority vote in Classification setting, or the mean of predicted value in regression setting.

Conditional Inference (CI) Tree is a Machine Learning method that learns a classifier in the form of a Binary Tree. The CI Tree, like most tree based methods, recursively partitions the feature space to make each sub-space as pure (single class) as possible. The CI Tree method need not require tree pruning. The other tree based methods first learn a tree with exhaustive search and then "prune" the tree in a post-hoc manner in order to reduce (ideally eliminate) over fitting. The CI Tree method leverages early-stopping criteria based on a permutation test, which does not make any assumption about the distribution of the data. The conditional inference framework allows splitting on categorical features in an un-biased manner. Most other tree based methods have a bias towards splitting on continuous features, or on features with many possible values.

Clustering algorithms discover groups of similar instances, instead of requiring a pre-defined classification. Clustering can be relevant when the training set instances do not have pre-defined class labels assigned to them. Several clustering techniques have been explored—e.g., Principal Component Analysis (PCA), Quality-Threshold Clustering. Clustering methods could be applicable in this context such as Random Forests (mentioned above), and Adaptive Resonance Clustering.

In accordance with some embodiments, a computer program application stored in non-volatile memory or computer-readable medium (e.g., register memory, processor cache, RAM, ROM, hard drive, flash memory, CD ROM, magnetic media, etc.) may include code or executable instructions that when executed may instruct and/or cause a controller or processor to perform methods discussed herein such as a method for evaluation of arrhythmia alarms based on asynchrony between ECGHR and ABPHR as described above.

The computer-readable medium may be a non-transitory computer-readable media including all forms and types of memory and all computer-readable media except for a transitory, propagating signal. In one implementation, the non-volatile memory or computer-readable medium may be external memory.

Although specific hardware and methods have been described herein, note that any number of other configurations may be provided in accordance with embodiments of the invention. Thus, while there have been shown, described, and pointed out fundamental novel features of the invention, it will be understood that various omissions, substitutions, and changes in the form and details of the illustrated embodiments, and in their operation, may be made by those skilled in the art without departing from the spirit and scope of the invention. Substitutions of elements from one embodiment to another are also fully intended and contemplated. The invention is defined solely with regard to the claims appended hereto, and equivalents of the recitations therein.

The invention claimed is:

1. A method of evaluating arrhythmia alarms based on one patient's perfusion level, the method comprising:
   receiving a set of pulsatile cardiovascular signals and a set of electrocardiogram signals obtained from the one patient during a same time window;
   analyzing the set of electrocardiogram signals to determine if an arrhythmia event is indicated;
   if an arrhythmia event is indicated, the method including:
      analyzing the cardiovascular signal to determine a pulse rate;
      calculating a systolic ratio;
      comparing the systolic ratio to a first predetermined threshold;
      if the systolic ratio is less than or equal to the first predetermined threshold, then activating a non-perfusion alarm;
      if the systolic ratio is greater than the first predetermined threshold, then calculating a standard deviation of a rate differential between the heart rate and the pulse rate values;
      if the standard deviation is greater than a second predetermined threshold, then activating the non-perfusion alarm; and
      if the non-perfusion alarm is activated, then:
         classifying a severity of the non-perfusion alarm; and
         displaying the activated non-perfusion alarm and the severity classification on a clinician terminal display.

2. The method of claim 1, including assessing a signal quality of one or more signals providing the pulsatile cardiovascular signals and the electrocardiogram signals.

3. The method of claim 1, wherein the determination of a non-perfusion indication is based on whether a drop in arterial blood pressure occurred during the time window.

4. The method of claim 1, wherein the calculated systolic ratio is a ratio between a systolic prior to the arrhythmia event and a delta systolic ratio.

5. The method of claim 4, wherein the delta systolic ratio is a difference between a maximum and a minimum systolic ratio during the arrhythmia event.

6. The method of claim 1, including determining the severity based on data stored in a population data table.

7. The method of claim 6, the severity determining step including identifying statistical and temporal trends in the data of the population data table.

8. The method of claim 1, including:
   detecting an asynchrony between the heart rate and the pulse rate values; and
   classifying the severity based on a magnitude of the detected asynchrony.

9. A non-transitory computer readable medium having stored thereon instructions which when executed by a processor cause the processor to perform a method of evaluating arrhythmia alarms based on one patient's perfusion level, the method comprising:
   receiving a set of pulsatile cardiovascular signals and a set of electrocardiogram signals obtained from the one patient during a same time window;

analyzing the set of electrocardiogram signals to determine a heart rate and to determine if an arrhythmia event is indicated;

if an arrhythmia event is indicated, the method including:
analyzing the cardiovascular signal to determine a pulse rate;
calculating a systolic ratio;
comparing the systolic ratio to a first predetermined threshold;
if the systolic ratio is less than or equal to the first predetermined threshold, then activating a non-perfusion alarm;
if the systolic ratio is greater than the first predetermined threshold, then calculating a standard deviation of a rate differential between the heart rate and the pulse rate values;
if the standard deviation is greater than a second predetermined threshold, then activating the non-perfusion alarm; and
if the non-perfusion alarm is activated, then:
classifying a severity of the non-perfusion alarm; and
displaying the activated non-perfusion alarm and the severity classification on a clinician terminal display.

10. The non-transitory computer readable medium of claim 9, further including executable instructions to cause a processor to perform the step of assessing a signal quality of one or more signals providing the pulsatile cardiovascular signals and the electrocardiogram signals.

11. The non-transitory computer readable medium of claim 9, further including executable instructions to cause a processor to perform the step of classifying the severity of the non-perfusion alarm based on data stored in a population data table.

12. The non-transitory computer readable medium of claim 11, further including executable instructions to cause a processor to perform the step of identifying statistical and temporal trends in the data of the population data table.

13. The non-transitory computer readable medium of claim 9, further including executable instructions to cause a processor to perform the steps of:
detecting an asynchrony between the heart rate and the pulse rate values; and
classifying the severity based on a magnitude of the detected asynchrony.

14. A system of evaluating arrhythmia alarms based on one patient's perfusion level comprising:
a server;
an electronic communication network connected to the server;
a clinician terminal, the clinician terminal connected to the electronic communication network;
a database having a population data table, the database connected to the electronic communication network, wherein the server, the clinician terminal, and the database are in communication across the electronic communication network;
one or more patient monitors connected to the electronic communication network, the patient monitors configured to provide monitored information on at least a pulsatile cardiovascular signal and an electrocardiogram signal to at least one of the server, clinician terminal, and the database; and
computer executable instructions which when executed by a processor cause the processor to:
analyze a set of electrocardiogram signals to determine if an arrhythmia event is indicated;
if an arrhythmia event is indicated, the computer executable instructions cause the processor to:
analyze the cardiovascular signal to determine a pulse rate;
calculate a systolic ratio;
compare the systolic ratio to a first predetermined threshold;
if the systolic ratio is less than or equal to the first predetermined threshold, then activate a non-perfusion alarm;
if the systolic ratio is greater than the first predetermined threshold, then calculate a standard deviation of a rate differential between the heart rate and the pulse rate values;
if the standard deviation is greater than a second predetermined threshold, then activate the non-perfusion alarm; and
if the non-perfusion alarm is activated, then:
classify a severity of the non-perfusion alarm; and
display the activated non-perfusion alarm and the severity classification on a clinician terminal display.

15. The system of claim 14, the computer executable instructions cause the processor to assess a signal quality of one or more signals providing the pulsatile cardiovascular signals and the electrocardiogram signals.

16. The system of claim 14, the computer executable instructions cause the processor to classify the severity of the non-perfusion alarm based on data stored in a population data table.

17. The system of claim 16, the computer executable instructions cause the processor to identifying statistical and temporal trends in the data of the population data table.

18. The system of claim 14, the computer executable instructions cause the processor to:
detect an asynchrony between the heart rate and the pulse rate values; and
classify the severity based on a magnitude of the detected asynchrony.

19. The system of claim 14 including an electronic medical record server in communication with the database by at least one of across the electronic communication network and a local connection.

* * * * *